US007863238B2

(12) United States Patent
Tomatsu et al.

(10) Patent No.: US 7,863,238 B2
(45) Date of Patent: Jan. 4, 2011

(54) PROTEINS WITH AN ATTACHED SHORT PEPTIDE OF ACIDIC AMINO ACIDS

(75) Inventors: Shunji Tomatsu, Clayton, MO (US); Ken'ichi Miyamoto, Ishikawa (JP); Masamichi Yamada, Hyogo (JP); Yasuhiro Tosaka, Hyogo (JP); Mana Yamada, Hyogo (JP)

(73) Assignees: Saint Louis University, St. Louis, MO (US); Kanazawa University, Kanazawa, Ishikawa (JP); JCR Pharmaceuticals Co., Ltd., Ashiya (JP)

( * ) Notice: Subject to any disclaimer, the term of this patent is extended or adjusted under 35 U.S.C. 154(b) by 434 days.

(21) Appl. No.: 10/864,758

(22) Filed: Jun. 10, 2004

(65) Prior Publication Data

US 2005/0276796 A1 Dec. 15, 2005

(51) Int. Cl.
*A61K 38/00* (2006.01)
(52) U.S. Cl. ......................................................... 514/2
(58) Field of Classification Search ........................ None
See application file for complete search history.

(56) References Cited

U.S. PATENT DOCUMENTS

2002/0169125 A1* 11/2002 Leung et al. .................. 514/12

FOREIGN PATENT DOCUMENTS

JP       2003-289882    * 10/2003
WO     WO 95/09611 A3    4/1995

OTHER PUBLICATIONS

Toietta G, et al "Various cells retrovirally transduced with N-acetylgalactosoamine-6-sulfate sulfatase correct Morquio skin fibroblasts in vitro," Hum Gene Ther. Nov. 1, 2001;12(16):2007-16.*
Biocompare, pFLAG-CTC Expression Vector from Sigma Aldritch, 1999-2009, pp. 1-2.*
Bernardi, "Chromatography of Proteins on Hydroxyapatite", Methods Enzymol 27:471-9 (1973).
Fujisawa, et al.: "Acidic Amino Acid-Rich Sequences as Binding Sites of Osteonectin to Hydroxyapatite Crystals" Biochim Biophys Acta 41292:53-60 (1996).
Kazuko, et al.: "Type IV Mucopolysaccharidosis (Morquio Syndrome), Congenital Metabolic Disorder Syndromes", Japanese Journal of Clinical Medicine, Suppl. No. 2, p. 442-445 (1998).
Niwa, et al: "Efficient Selection for High-Expression Transfectants With a Novel Eukaryotic Vector" Gene 108:193-200 (1991).
Tomatsu, et al.: "Morquio Disease: Isolation, Characterization and Expression of Full-Length CDNA for Human N-Acetylgalactosamine-6-Sulfate Sulfatase" Biochem. Biophys. Res. Commun. 181:677-683 (1991).
Rose, et al.: "Primary Structure of the Human Melanoma Associated Antigen p97 (Melanotransferrin) Deduced From the MRNA Sequence" Proc. Natl. Acad. Sci. USA, 83:1261-1265 (1986).
Hall, C.W., et al., "α-L-Iduronidase Activity in Cultured Skin Fibroblasts and Amniotic Fluid Cells," Archives of Biochemistry and Biophysics, 158, pp. 817-821 (1973).
Achord, D.T., et al., "Human β-Glucuronidase: In Vivo Clearance and in Vitro Uptake by a Glycoprotein Recognition System on Reticuloendothelial Cells," Cell, vol. 15, pp. 269-278, Sep. 1978.
Oldberg, A., et al., "The Primary Structure of a Cell-Binding Bone Sialoprotein," The Jrnl of Biological Chem., vol. 263, No. 36, pp. 19430-19432, Dec. 25, 1988.
Kasugai, S., et al., "Selective Drug Delivery System to Bone: Small Peptide $(Asp)_6$ Conjugation," Jrnl of Bone and Mineral Research, vol. 15, No. 5, pp. 936-943, 2000.
Nagata, T., et al., "Biosynthesis of Bone Proteins [SPP-1 (secreted phosphoprotein-1, osteopontin), BSP (bone sialoprotein) and SPARC (osteonectin)] in association with mineralized-tissue formation by fetal-rat calvarial cells in culture," Biochem. J. vol. 274, pp. 513-520, (1991).
Sekido, T., et al., "Novel Drug Delivery System to Bone Using Acidic Oligopeptide: Pharmacokinetic Characteristics and Pharmacological Potential," J. of Drug Targeting, vol. 9, No. 2, pp. 111-121, 2001.
Yokogawa, K., et al., "Selective Delivery of Estradiol to Bone by Aspartic Acid Oligopeptide and Its Effects on Ovariectomized Mice," Endocrinology, vol. 142, No. 3, pp. 1228-1233.
Masue, M., et al., "N-Acetylgalactosamine-6-Sulfate Sulfatase in Human Placenta: Purification and Characteristics[1]," J. Biochem. vol. 110, No. 6, pp. 965-970, 1991.
Tomatsu, S., et al., "Morquio Disease: Isolation, Characterization and Expression of Full-Length cDNA for Human N-Acetylgalactosamine-6-Sulfate Sulfatase," Biochemical and Biophysical Research Communications, vol. 181, No. 2, pp. 677-683, Dec. 16, 1991.
Tomatsu, S., et al., "Mouse model of N-acetylgalactosamine-6-sulfate sulfatase deficiency $(Gains^{-1-})$ produced by targeted disruption of the gene defective in Morquio A disease," Human Molecular Genetics, vol. 12, No. 24, pp. 3349-3358, 2003.
Fujisawa et al. "Acidic Homopolypeptides as Models for Hydroxyapatite-Binding Sites of Non-collagenous Proteins in Bone and Tooth", Department of Biochemistry, School of Dentistry, Hokkadido University; Connective Tissue Research, vol. 33, Apr. 11, 2001.
Fujisawa et al. "Attachment of Osteoblastic Cells to Hydoxyapatite Crystals by a Synthetic Peptide $(Glu_7-Pro-Arg-Gly-Asp-Thr)$ Containing Two Functional Sequences of Bone Sialoprotein" Matrix Biology vol. 16, pp. 21-28, 1997.
Goldberg et al. "Binding of Bone Sialoprotein, Osteopontin and Synthetic Polypeptides to Hydroxyapatite" Connective Tissue Research, vol. 42, No. 1, pp. 25-37, Dec. 21, 1999.

* cited by examiner

*Primary Examiner*—Cecilia Tsang
*Assistant Examiner*—Thomas S Heard
(74) *Attorney, Agent, or Firm*—Millen, White, Zelano & Branigan, P.C.

(57) ABSTRACT

Disclosed are a fusion protein comprising enzyme N-acetylgalactosamine-6-sulfate sulfatase and a short peptide consisting of 4-15 acidic amino acids attached to the enzyme on its N-terminal side, a pharmaceutical composition containing the fusion protein, and a method for treatment of type A Morquio disease using the fusion protein. Compared with the native enzyme protein, the fusion protein exhibits higher transferability to bone tissues and improved, higher stability in the blood.

7 Claims, 6 Drawing Sheets

A Native GALNS

B NBT-GALNS

PROTEINS WITH AN ATTACHED SHORT PEPTIDE OF ACIDIC AMINO ACIDS

TECHNICAL FIELD

The present invention relates to endowing a protein with in vivo bone-tissue targeting ability and improvement of its stability in the blood. More specifically, the present invention relates to endowing a protein with bone-tissue targeting ability and improvement of its stability by means of addition of a short peptide consisting of acidic amino acids to the N-terminus of the protein.

BACKGROUND ART

It has been reported that acidic peptide chains consisting of aspartic acid and/or glutamic acid molecules have high bonding affinities for hydroxyapatite, one of the component materials of the bone (1, 2). Making use of this property, techniques have been reported by which those acidic peptide chains are attached to steroid hormones (sex hormones or protein anabolic hormones, etc.), which are used for bone diseases such as osteoporosis, for endowing those steroid hormones with bone-tissue targeting ability (Japanese Patent Application Publication No. 2000-327583)(3). Further techniques have been reported by which peptide chains made of carboxylated amino acid derivatives having three or more carboxyl groups per molecule were attached to and used as bone-targeting, drug-transporting carriers for steroid hormones, methotrexate, anti-cancer antibiotics, alkylating agents or cell growth factors (Japanese Patent Application Publication No. 2002-3407)(4).

Meanwhile, there is a problem that pharmaceutical preparations of physiologically active proteins like enzymes and peptide hormones are generally made unstable when they are administered to the body, and thus undergo relatively rapid inactivation by, e.g., enzymatic degradation. For stabilizing pharmaceutical preparations of physiologically active proteins in the body, a method is known which is based on coupling the proteins to polyethylene glycol (Japanese Patent No. 2852127)(5).

Among numbers of diseases caused by congenital anomaly, there is type IV A mucopolysaccharidosis (hereinafter referred to as type A Morquio disease). In mucopolysaccharidosis, which forms a group of lysosomal diseases caused by a deficiency of enzymes necessary for the metabolism of glycosaminoglycan (hereinafter referred to as GAG), accumulation of GAG occurs in affected part of the tissue as a result of the deficiency of that enzyme. Although its clinical symptoms vary among individual patients, its common characteristic pathologies include swelling of cells caused by the accumulation of GAG in lysosomes, hypertrophy of organs, destruction of tissues and failing organs. Progressive accumulation of GAG is noted and clinical symptoms are, in majority of cases, also chronic and progressive.

Type A Morquio disease is an autosomal recessive genetic disease caused by an anomaly in the gene for a lysosomal enzyme, N-acetylgalactosamine-6-sulfate sulfatase (hereinafter referred to as GALNS) and is classified as type IV A mucopolysaccharidosis. GALNS is an enzyme that hydrolyses the sulfate groups of chondroitin-6-sulfate and keratan sulfate, which are species of GAG, and the deficiency of the enzyme causes intra-tissue deposition of GAG and its increased excretion in the urine. One of the clinical characteristics of Type A Morquio disease is bone dysplasia, and thus short statute, scoliokyphasis, brevicollis, coxa valga, and articular hyperextension have been reported to occur. Also reported are corneal opacity, deafness and cardiac valvular disorders. On the one hand, one of its characteristics that is quite different from Hunter's syndrome and Hurler's syndrome is that no psychomotor retardation is observed in patients with type A Morquio disease (6).

No effective remedy is currently available for type A Morquio disease, and bone marrow transplantation provides no more than a marginal improvement of osteopathy. Thus, most of its treatment is addressed to symptomatic therapy or control of symptoms, like orthopaedic treatment to prevent dislocation in upper cervical vertebrae. On the other hand, as main symptoms are localized in the bone and joints in type A Morquio disease, it is expected that the quality of life of the patients could be greatly improved if their osteopathy is alleviated. While substitution therapy with enzyme GALNS is contemplated for type A Morquio disease, substitution therapy using native GALNS is not expected to give any satisfactory effect considering its rapid inactivation in the body and low rate of its transfer to bone tissues including growing cartilage.

DISCLOSURE OF INVENTION

Against the above-mentioned background, an objective of the present invention is to achieve increased rate of delivery, to bone tissues, of physiologically active proteins such as enzymes to be administered to a patient, through endowing them with a targeting ability to that tissue.

Another objective of the present invention is to increase in vivo stability of physiologically active proteins administered to a patient such as enzymes. When an acidic short peptide was attached to the N-terminus of enzyme GALNS, the inventors found that it unexpectedly improved in great deal the in vivo stability of GALNS and allowed notable transfer of GALNS to bone tissues. The present invention was completed upon the findings.

Thus, the present invention provides:

1. A fusion protein comprising
   a physiologically active protein and
   a short peptide which consists of 4-15 acidic amino acids and is attached to the physiologically active protein on the N-terminal side thereof.

2. The fusion protein according to 1 above, wherein the physiologically active protein is an enzyme protein.

3. The fusion protein according to 1 above, wherein the physiologically active protein is N-acetylgalactosamine-6-sulfate sulfatase.

4. The fusion protein according to one of 1 to 3 above, wherein the short peptide is attached to the N-terminus of the physiologically active peptide via a linker peptide.

5. A method for enhancing the transferability of a physiologically active protein from the blood to bone tissues, wherein the method comprises converting the physiologically active protein into a fusion protein comprising the physiologically active protein and a short peptide which consists of 4-15 acidic amino acids and is attached to the physiologically active protein on the N-terminal side thereof.

6. The method according to 5 above, wherein the physiologically active protein is an enzyme protein.

7. The method according to 5 above, wherein the physiologically active protein is N-acetylgalactosamine-6-sulfate sulfatase.

8. The method according to one of 5 to 7 above, wherein the short peptide is attached to the N-terminus of the physiologically active peptide via a linker peptide.

9. A method for increasing the stability of a physiologically active protein in the blood, wherein the method comprises converting the physiologically active protein into a fusion protein comprising the physiologically active protein and a short peptide which consists of 4-15 acidic amino acids and is attached to the physiologically active protein on the N-terminal side thereof.

10. The method of according to 9 above, wherein the physiologically active protein is an enzyme.

11. The method according to 9 above, wherein the physiologically active protein is N-acetylgalactosamine-6-sulfate sulfatase.

12. The method according to one of 9 to 11 above, wherein the short peptide is attached to the N-terminus of the physiologically active peptide via a linker peptide.

13. A pharmaceutical composition comprising a fusion protein comprising

N-acetylgalactosamine-6-sulfate sulfatase and a short peptide which consists of 4-15 acidic amino acids and is attached to N-acetylgalactosamine-6-sulfate sulfatase on the N-terminal side thereof.

14. The pharmaceutical composition according to 13 above, wherein the short peptide is attached to the N-terminus of the physiologically active protein via a linker peptide.

15. A method for treatment of type A Morquio disease, comprising administering to a human patient therewith a therapeutically effective amount of a fusion protein comprising N-acetylgalactosamine-6-sulfate sulfatase and a short peptide which consists of 4-15 acidic amino acids and is attached to N-acetylgalactosamine-6-sulfate sulfatase on the N-terminal side thereof.

16. The method for treatment according to 15 above, wherein the short peptide is attached to the N-terminus of N-acetylgalactosamine-6-sulfate sulfatase via a linker peptide.

Comparing with native physiologically active proteins, the present invention described above provides physiologically active fusion proteins with increased stability in the blood when administered to a patient such as a human patient as well as enhanced targeting ability to bone tissues, and, in particular, a GALNS fusion protein modified in such a manner, and further provides a pharmaceutical composition useful for the treatment of type A Morquio disease, as well as a method for the treatment of type A Morquio disease.

BEST MODE FOR CARRYING OUT THE INVENTION

Figure 1:
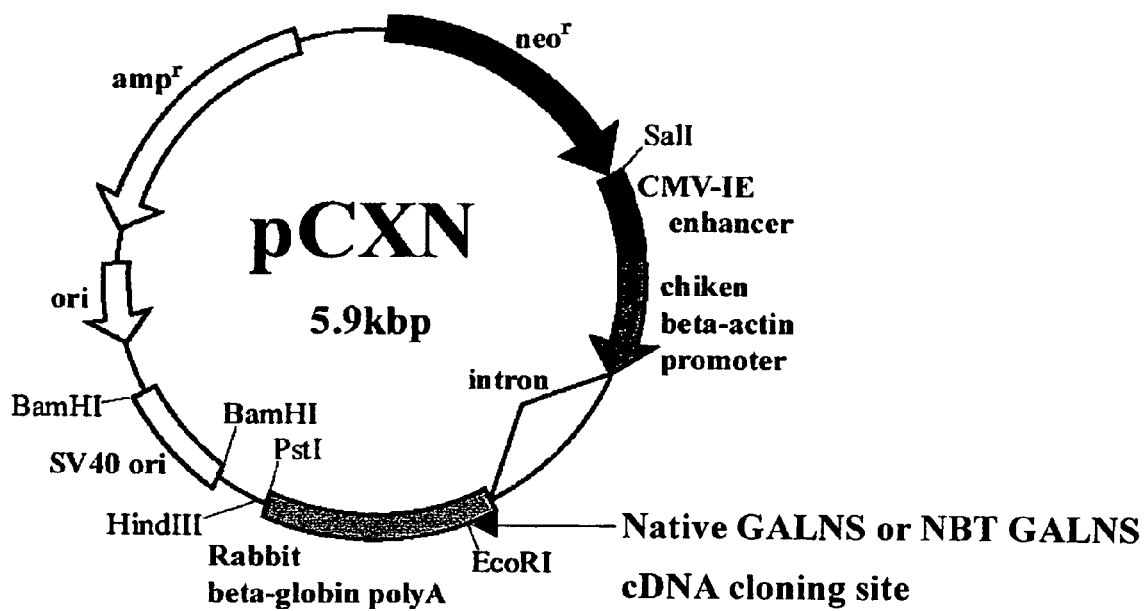
FIG. 1 is a schematic diagram illustrating pCXN vector and the cloning site in the vector for the cDNA encoding native GALNS or the GALNS fusion protein.

The term "acidic amino acid" referred to in the present invention means glutamic acid or aspartic acid. As the employment of these acidic amino acids in the present invention are for the purpose of constructing an acidic short peptide, they may be used in any arbitrary combination including a simple use of one or the other of them alone for the construction of such a short peptide. The number of the acidic amino acids forming a short peptide is preferably 4-15, more preferably 4-12, and still more preferably 4-8.

A short peptide consisting of acidic amino acids may be directly attached to the N-terminus of a physiologically active protein via a peptide bond or the like, or, instead, it may be attached via a linker peptide.

In the present invention, "a linker peptide" is not an indispensable component, for it is usable only for convenience in attaching a short peptide consisting of acidic amino acids to the N-terminus of a physiologically active protein. Where it is used, a linker peptide may be a short peptide consisting, e.g., preferably of 15 or less, more preferably of 10 or less, and still more preferably of 6 or less amino acids. Such a linker that consists of a single amino acid molecule and linking between the acidic short peptide and the physiologically active protein via peptide bonds is also included in the definition of a linker peptide. A linker peptide may be made of any one or more amino acids as desired.

In the present invention, though there is no specific limitation as to the method for attaching an acidic short peptide and a physiologically active protein, it is of advantage, e.g., to form and use a transformant cell expressing the fusion protein consisting of the short peptide and the physiologically active protein.

A fusion protein of the present invention may include a non-acidic amino acid or a sequence of several (e.g., 3) non-acidic amino acids at the N-terminus of the short peptide consisting of acidic amino acids.

A fusion protein of the present invention, in particular a fusion protein comprising enzyme N-acetylgalactosamine-6-sulfate sulfatase and a short peptide, may be prepared in the form of a pharmaceutical composition containing the fusion protein dissolved or dispersed in a pharmaceutically acceptable carrier well known to those who are skilled in the art, for parenteral administration by, e.g., intravenous, subcutaneous or intramuscular injection or by intravenous drip infusion.

For a pharmaceutical composition for parenteral administration, any conventional additives may be used such as excipients, binders, disintegrants, dispersing agents, lubricants, diluents, absorption enhancers, buffering agents, surfactants, solubilizing agents, preservatives, emulsifiers, isotonizers, stabilizers, solubilizers for injection, pH adjusting agents, etc.

A fusion protein of the present invention, in particular a fusion protein comprising enzyme N-acetylgalactosamine-6-sulfate sulfatase and a short peptide, may be used advantageously in place of the conventional native enzyme in a substitution therapy for the treatment of type A Morquio disease. In the treatment, the fusion protein may be administered intravenously, subcutaneously or intramuscularly. Doses and frequencies of administration is to be determined by the physician in charge in accordance with the condition of his or her patient.

EXAMPLES

Method for Construction of Expression Vector

Figure 2:
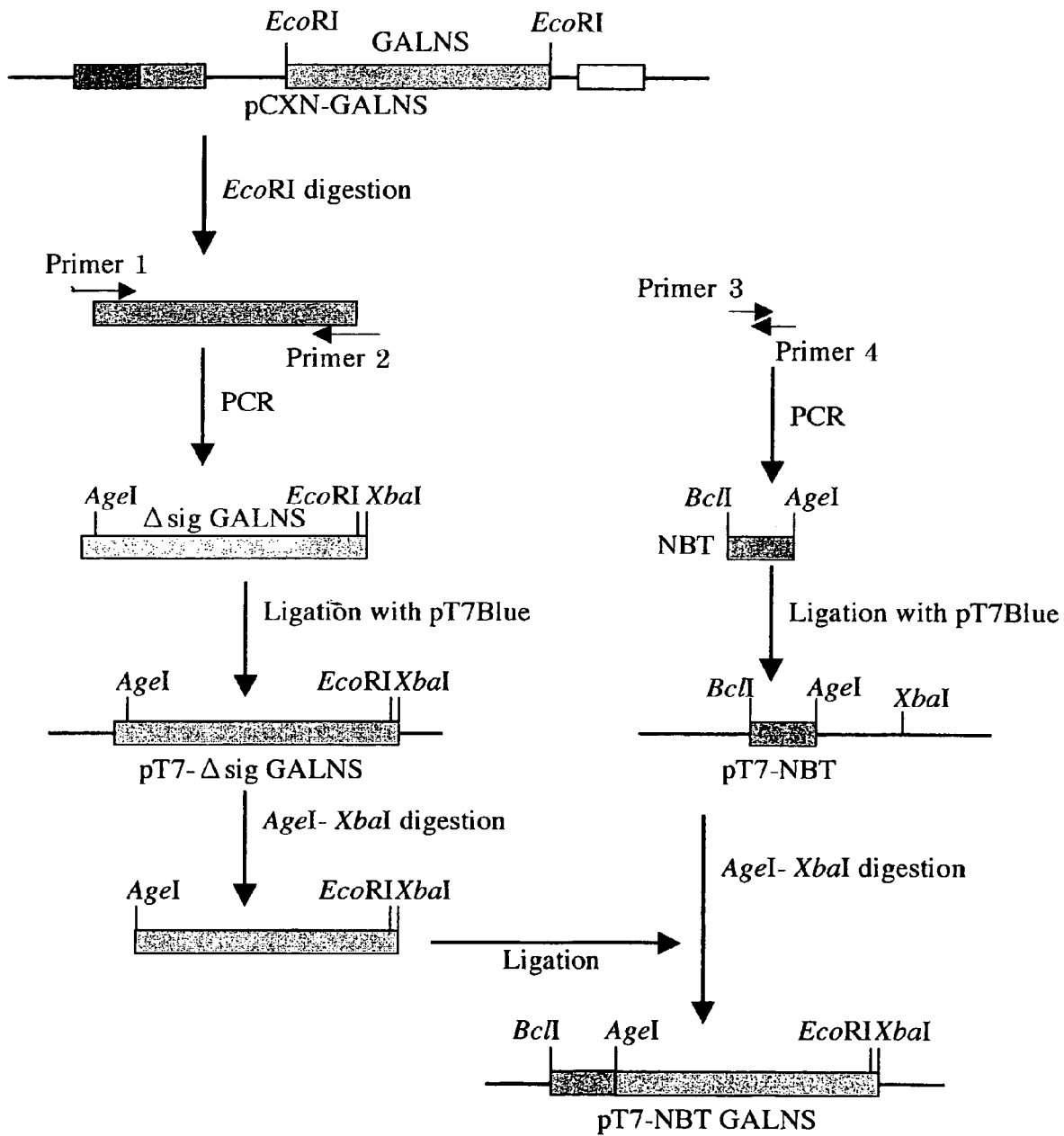
FIG. 2 illustrates a first half group of the steps for the construction of an expression vector pCXN-p97-NBT-GALNS used for the production of a GALNS fusion protein.
Figure 3:
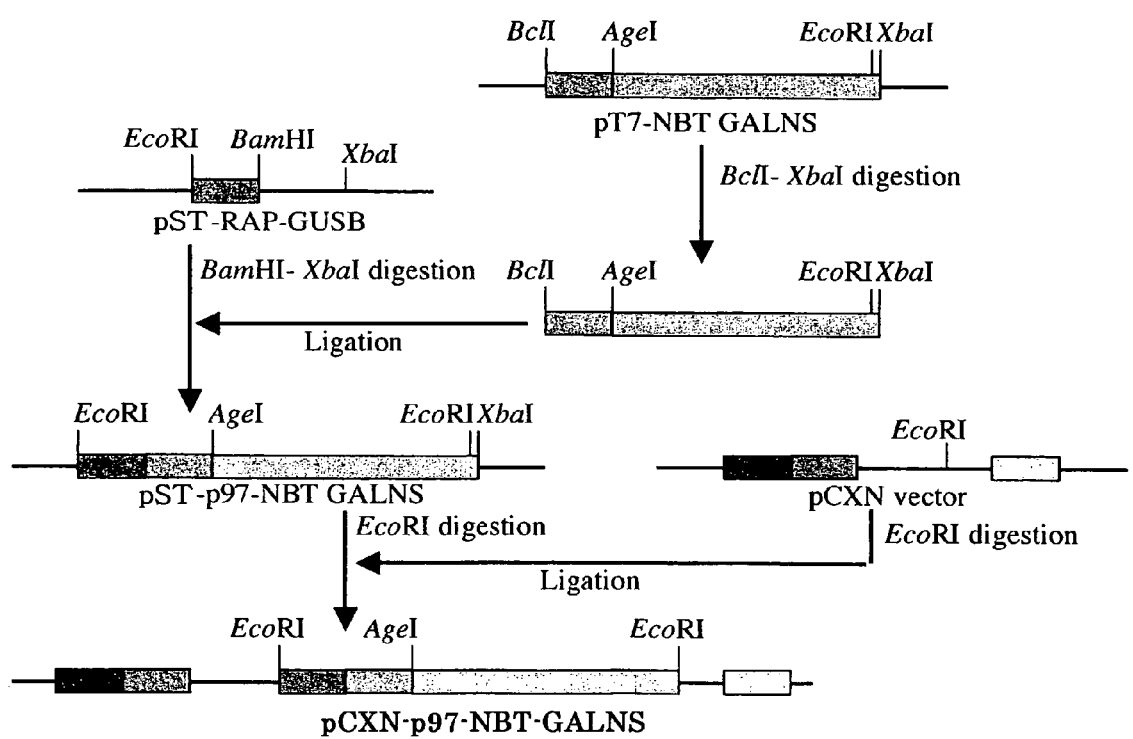
FIG. 3 illustrates a second half group of the steps for the construction of an expression vector pCXN-p97-NBT-GALNS used for the production of the GALNS fusion protein.

Vector pCXN had been constructed in accordance with a literature (7) and was offered to us by Prof. Miyazaki at Osaka University. An expression vector for native human GALNS, pCXN-GALNS, was one that had been reported by Tomatsu et al. in 1991 (8). An expression vector for human GALNS to the N-terminus of which is attached (via a linker peptide) a short peptide (N-terminal bone tag: NBT) consisting of acidic amino acids (NBT-GALNS) was constructed starting with pCXN-GALNS in the following manner. FIGS. 2 and 3 schematically illustrate the process for construction.

By cleaving pCXN-GALNS with EcoRI, human GALNS cDNA was recovered. Using this as a template, PCR was carried out using IA-Taq (Takara) to amplify Δsig GALNS cDNA (nt 79-1569 in SEQ ID NO:1, which is the sequence left after removal of nt 1-78 corresponding to the secretion signal from the ORF region.) to the 5'-terminus of which is attached an AgeI cleavage sequence. The PCR was carried out according to the instruction for use of LA-Taq, i.e., through the cycles consisting of 30 seconds at 94° C., (30 seconds at 94° C., 30 seconds at 60° C., and 2 minutes at 72° C.)×25, and then 3 minutes at 72° C., with primer 1 (SEQ ID NO:2) and primer 2 (SEQ ID NO:3). The cDNA thus amplified was inserted into the pT7Blue vector (Novagen) to construct pT7-Δsig GALNS.

An N-terminal bone tag (NBT) cDNA to be attached to the 5'-terminus then was constructed by PCR using LA-Taq (Takara). Briefly, employing primer 3 (SEQ ID NO:4) and primer 4 (SEQ ID NO:5), which contained portions that were complementary to each other, PCR was performed through the cycles of 30 seconds at 94° C., (30 seconds at 94° C., 30 seconds at 60° C., and 30 seconds at 72° C.)×20, and then one minute at 72° C. The cDNA thus amplified was cloned into the pT7Blue vector to construct pT7-NBT.

A human GALNS cDNA recovered as a fragment of pT7-Δsig GALNS cleaved with AgeI and XbaI was inserted into the AgeI-XbaI site of pT7-NBT to construct pT7-NBT-GALNS. Then, pT7-NBT-GALNS was cleaved with BclI, blunt-ended with T4 DNA polymerase by addition of nucleotides to its sticky ends, and cleaved with XbaI to recover the NBT-GALNS cDNA.

pST-RAP-GUSB (A vector containing the p97 signal sequence. This was provided by Tomatsu at Saint Louis University) was cleaved with BamHI and XbaI, into which then was inserted the NBT-GALNS cDNA recovered above to construct pST-p97-NBT-GALNS.

pST-p97-NBT-GALNS was cleaved with EcoRI to recover the p97-NBT-GALNS cDNA, which then was inserted into the EcoRI site of pCXN to construct an NBT-GALNS expression vector, pCXN-p97-NBT-GALNS. The DNA sequence of the region containing the NBT-GALNS cDNA of the expression vector and the corresponding amino acid sequence are shown as SEQ ID NOs:6 and 7, respectively.

SEQ ID NO:6 is part of the sequence containing the NBT-GALNS cDNA of pCXN-p97-NBT-GALNS. Nt 13-19 encode the p97 signal sequence, nt 73-90 a poly Glu, nt 91-108 a linker sequence, and nt 109-1596 GALNS without the signal sequence.

SEQ ID NO:7 is the NBT-GALNS with the p97 signal sequence. Aa 1-19: p97 signal sequence, aa 21-26: poly Glu, aa 27-32: linker sequence, aa 33-528: GALNS without signal sequence.

The protein set forth as SEQ ID NO:7 contains the p97 secretion signal sequence. The signal sequence is removed during secretion process from the cell and a fusion protein consisting of aa 20-528 is thus recovered as NBT-GALNS in the medium.

P97 is a cell-surface glycoprotein occurring most human melanomas and its signal sequence consists of 19 amino acids (9). The aforementioned pCXN-p97-NBT-GALNS containing the cDNA encoding this signal sequence may also be constructed by the following method. Briefly, a cDNA containing the p97 signal sequence is synthesized through the process of primers annealing and PCR amplification. LA-Taq is used as an enzyme for PCR. As primers having mutually complementary portions, primer 4 (SEQ ID NO:8) and primer 5 (SEQ ID NO:9) are used. PCR is performed through the cycles of 30 seconds at 94° C., (30 seconds at 94° C., 30 seconds at 60° C., 30 seconds at 72° C.)×20, and one minute at 72° C. The amplified cDNA containing the p97 signal sequence is cleaved with BamHI and EcoRI. The pCXN vector is cleaved with EcoRI, into which are simultaneously incorporated the aforementioned NBT-GALNS cDNA recovered after the enzyme treatment and the cDNA for the p97 signal sequence to construct pCXN-p97-NBT-GALNS.

SEQ ID NO:8 is a forward primer 5, in which nt 1-5 comprise a random synthetic sequence, and nt 6-52 comprise part of the sequence encoding p97 signal.

SEQ ID NO:9 is a reverse primer, in which nt 1-6 comprise a random sequence, and nt 7-51 comprise part of the sequence encoding p97 signal.

[Establishment of Expression Cell]

Nunclon ΔMultiDish 6 Well was inoculated with CHO-K1 cells. After an overnight culture in DMEM/F12/FBS medium, either pCXN-p97-NBT-GALNS or pCXN-GALNS was introduced into the cells using the Lipofectamine 2000 reagent. For experimental procedures, the instruction manual attached to the Lipofectamine 2000 reagent was followed. After a two-day incubation at 37° C. in 5% $CO_2$, the cells were added to 75-cm$^2$ tissue culture flasks (Iwaki) and incubated until colonies of resistant cells were formed with Geneticin (Gibco) added to the DMEM/F12/FBS medium at the final concentration of 1 mg/mL. After formation of colonies was confirmed under a microscope, cells which exhibited stable expression were cloned by the limiting dilution-culture method. Screening for expression cells were performed by sulfatase assay of the culture supernatants. The NBT-GALNS expression cell line was designated CHO-NBT-GALNS40, and the human native GALNS expression cell line CHO-GALNS14. The established cell lines were subcultured in the DMEM/F12 medium (Gibco) supplemented with 10% fetal bovine serum (Thermo Trace) and 0.2 mg/mL Geneticin.

[Culture of Cells Expressing NBT-GALNS and GALNS]

CHO-GALNS 14 cells (cells expressing human native GALNS) and CHO-NBT-GALNS 40 cells (cells expressing NBT-attached human GALNS) were cultured as follows. Briefly, a DMEM/F12 medium (Gibco) supplemented with 10% fetal bovine serum (Thermo Trace) and 0.2 mg/mL geneticin was used as the subcultivation medium (DMEM/F12/FBS/G), and a EX-CELL 325 PF medium containing 2 mM glutamine, 10 mg/L hypoxantine and 4 mg/L thymidine was used as the production medium (EX-CELL 325 G/H/T). All the cultivation was performed at 37° C. in 5% $CO_2$. Cells in DMEM/F12/FBS were added to 18 of 225 cm$^2$ tissue culture flasks (Iwaki) and cultured overnight so that 80-100% confluency would be reached the following day. The culture supernatant was removed and the cells were washed twice with PBS(−). After the medium was replaced with about 50 mL/flask of EX-CELL 325 G/H/T, culture was continued for three days. The culture supernatant was recovered and immediately frozen at −20° C. and stored. All the cells were detached with 0.25% Trypsin-EDTA (Gibco), suspended in 5 L of DMEM/F12/FBS, added evenly to 48 of Nunclon ΔTriple Flasks (Nunc) and cultured overnight. The culture supernatant was removed, and the cells washed twice with PBS(−). After the medium was replaced with about 100 mL/flask of EX-CELL 325 G/H/T, culture was continued for 3 days. The culture supernatant was recovered and immediately frozen and stored at −20° C. Following the above procedures, 6 L of culture supernatant was recovered per operation.

[Purification of Native GALNS]

The aforementioned culture supernatant was thawed in a water bath, and filtered through a 0.22 μm polyethersulfone membrane (1000 mL Filter System, Corning Inc.) to remove insoluble contaminants in the culture supernatant. The filtered culture supernatant was concentrated 20-fold by ultrafiltration using regenerated cellulose membrane (Prep/Scale-TFF-1 30 kDa MWCO, MILLIPORE Corporation). In preparation for ion-exchange chromatography, the concentrated culture supernatant was then dialyzed against 20 mM Tris-HCl, 50 mM NaCl, pH 7.8.

The buffer-exchanged and concentrated culture supernatant was loaded onto a HiPrep DEAE 16/10 DEAE FF column (Amersham Biosciences)(bed volume: 20 mL) that had been equilibrated with 20 mM Tris-HCl, 50 mM NaCl, pH 7.8. After washing the column with the equilibration buffer, fractions that were eluted with 20 mM Tris-HCl, 150 mM NaCl, pH 7.8 (flow rate: 5 mL/min) were collected.

In preparation for Q Sepharose chromatography, the collected fractions were dialyzed against a dialysate of 10 mM MES, 50 mM NaCl, pH 5.5. The fractions collected by DEAE Sepharose chromatography and buffer-exchanged were loaded onto a HiPrep Q 16/10 Q FF column (Amersham Biosciences)(bed volume: 20 mL) that had been equilibrated with 10 mM ES, 50 mM NaCl, pH 5.5 and passing through fractions were collected (flow rate: 5 mL/min). The column was washed with the equilibration buffer and washing fractions were also collected (flow rate: 5 mL/min).

In preparation for Sephacryl S-200 chromatography, the collected fractions were concentrated by ultrafiltration using regenerated cellulose membrane (Amicon Ultra-15, 30 kDa MWCO). The concentrated fractions collected by the Q Sepharose chromatography were loaded onto a HiPrep 16/60 Sephacryl S-200 HR column (Amersham Biosciences) that had been equilibrated with 10 mM MES, 150 mM NaCl, pH 5.5 and fractions corresponding to the aimed peak were collected.

Figure 4:
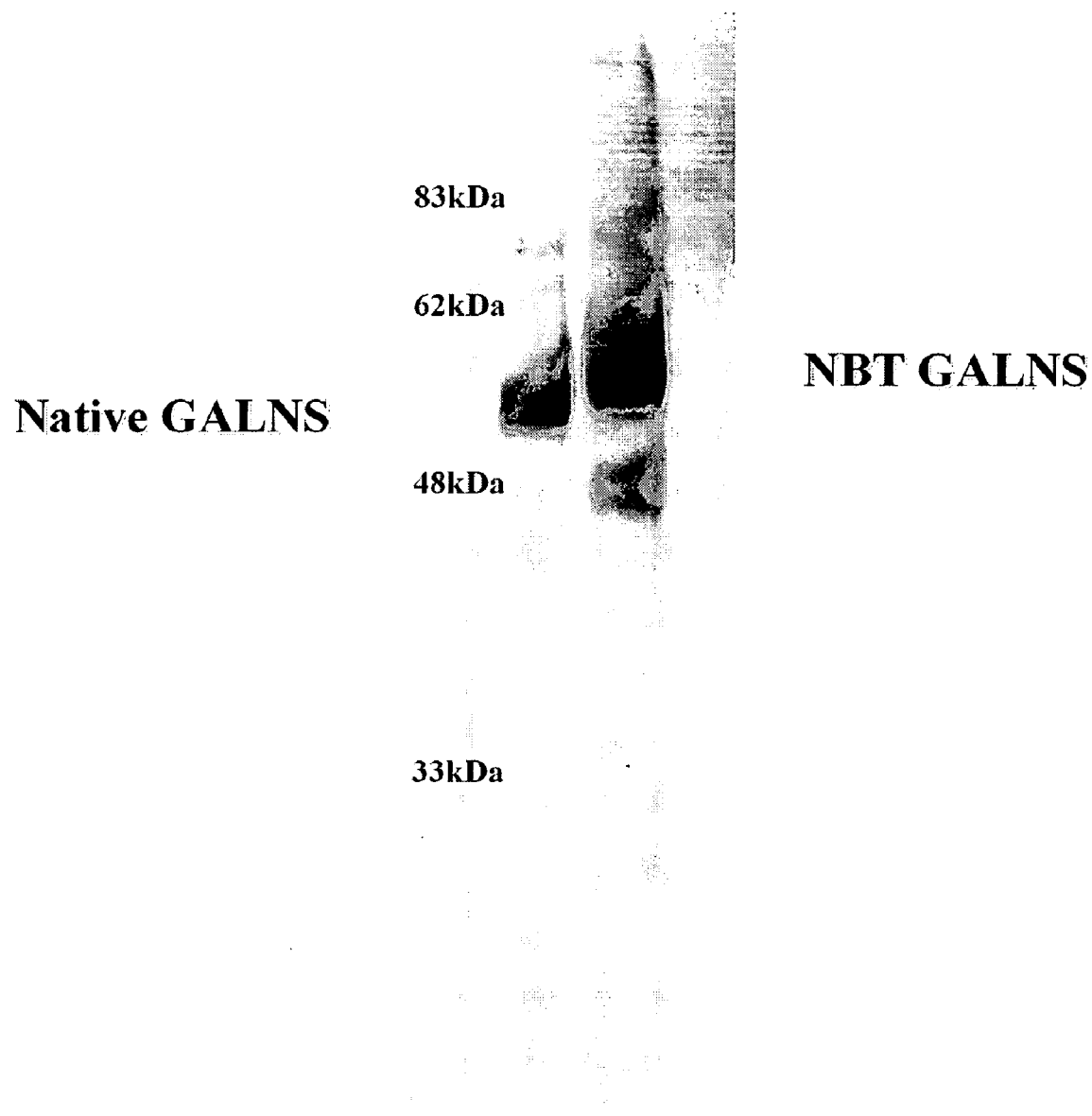
FIG. 4 shows the result of SDS-PAGE analysis of purified native GALNS and the GALNS fusion protein.

SDS-PAGE gel electrophoresis of the NBT-GALNS collected through the steps described above confirmed that it had been purified enough to appear as a single band (FIG. 4).

At each step of the purification, fractions containing native GALNS were detected by sulfate assay described later.

[Purification of NBT-GALNS]

As NBT-GALNS was expected to differ from native GALNS in physicochemical properties and have a high affinity for hydroxyapatite, it was purified by a method described below which included hydroxyapatite chromatography.

The aforementioned culture supernatant was thawed in a water bath, and filtered through a 0.22 μm polyethersulfone membrane (1000 mL Filter System, Corning Inc.) to remove insoluble contaminants in the culture supernatant. The filtered culture supernatant was concentrated 20-fold by ultrafiltration using regenerated cellulose membrane (Prep/Scale-TFF-1 30 kDa MWCO, MILLIPORE Corporation). In preparation for ion-exchange chromatography, the concentrated culture supernatant was then dialyzed against a dialysate of 20 mM Tris-HCl, 50 mM NaCl, pH 7.8.

The buffer-exchanged and concentrated culture supernatant was loaded onto a HiPrep DEAE 16/10 DEAE FF column (Amersham Biosciences)(bed volume: 20 mL) that had been equilibrated with 20 mM Tris-HCl, 50 mM NaCl, pH 7.8. After washing the column with the equilibration buffer, fractions that were eluted with 20 mM Tris-HCl, 150 mM NaCl, pH 7.8 (flow rate: 5 mL/min) were collected. In preparation for Q Sepharose chromatography, the collected fractions were dialyzed against 10 mM MES, 50 mM NaCl, pH 5.5 for buffer exchange.

The fractions collected by DEAE Sepharose chromatography and buffer-exchanged were loaded onto a HiPrep Q 16/10 Q FF column (Amersham Biosciences)(bed volume: 20 mL) that had been equilibrated with 10 mM ES, 50 mM NaCl, pH 5.5. After washing the column with the equilibration buffer, fractions eluted with 10 mM MES, 250 mM NaCl, pH 5.5 were collected (flow rate: 5 mL/min).

Fractions collected by Q Sepharose chromatography were loaded onto a hydroxyapatite column, Econo-Pac CHT-II cartridge column (Bio-Rad)(bed volume: 5 mL) that had bee equilibrated with 1 mM phosphate buffer, 10 mM MES, 50 mM NaCl, pH 5.5. After washing the column with the equilibration buffer (flow rate: 0.5 mL/min), fractions eluted with 500 mM phosphate buffer, 10 mM MES, 50 mM NaCl, pH 5.5 was collected (flow rate: 0.5 mL/min). In preparation for Sephacryl S-200 chromatography, the collected fractions were concentrated by ultrafiltration using regenerated cellulose membrane (Amicon Ultra-15 30 kDa, MWCO).

The concentrated fractions obtained by CHT-II hydroxyapatite chromatography were loaded onto a HiPrep 16/60 Sephacryl S-200 HR column (Amersham Biosciences) that had been equilibrated with 10 mM MES, 150 mM NaCl, pH 5.5 and fractions corresponding to the aimed peak were collected.

SDS-PAGE gel electrophoresis of the NBT-GALNS collected through the steps described above confirmed that it had been purified enough to appear as a single band (FIG. 4).

At each step of the purification, fractions containing GALNS were detected by sulfate assay described below.

[Sulfate Assay]

To 10 μL of a sample was added 100 μL of a substrate solution [5 mM 4-methylumbelliferyl sulfate (Sigma), 5 mM sodium acetate (Wako Pure Chemical Industries), 0.05% BSA (Sigma), pH 4.4]. After one-hour reaction at 37° C., 190 μL of a stop solution [332 mM glycine (Wako Pure Chemical Industries), 208 mM sodium carbonate (Wako Pure Chemical Industries), pH 10.7] was added and fluorescence was measured on a fluorescence plate reader (Molecular Device) at the wavelengths of 460 nm (em)/355 nm (ex). As a control, 4-methylumbelliferone (Sigma) was used which was diluted with a solution prepared by mixing the substrate solution and the stop solution in the proportion described above. Starting with 1 mM, 7 steps of twofold dilution were made.

[SDS Polyacrylamide Gel Electrophoresis]

1) SDS Polyacrylamide Gel Electrophoresis and Staining

Samples were treated with SDS using Laemmli Sample Buffer (Bio-Rad) in the presence of 5% β-mercaptoethanol (Bio-Rad) and subjected to SDS-PAGE in PAG mini "DAIICHI" 12.5 (Daiichi Pure Chemicals). For staining, SYPRO RUBY GEL STAIN (Biorad) or 2D-silver stain reagent-II "DAIICHI" (Daiichi Pure Chemicals) was used.

[Preparation of Antibodies]

Polyclonal and monoclonal antibodies were prepared by a conventional method through immunization of mice with native GALNS as the antigen.

[Immunostaining of Bone Tissues]

GALNS or NBT-GALNS, both purified, was administered to four-month old male C57BL mice in the tail vein at a dose of 250 U/g body weight. Two hours after administration, tissue specimen slides were prepared for bone slices of the mice including femur, knee joint, and cervical vertebra. Briefly, the slide were immersed in a xylene bath for 3 minutes, taken out and then transferred to another xylene bath. This step was repeated 5 times. The xylene-treated slides were immersed in 99.5% ethanol for 3 minutes, taken out and then transferred to another ethanol bath. This step was repeated 3 times. The slides were washed 3 times in the same manner with 95% ethanol and immersed in a phosphate buffer for 15 minutes. The phosphate buffer was wiped out of the slides. The slices then were covered with methanol containing 3% hydrogen peroxide and allowed to stand for 5 minutes at room temperature to inactivate intrinsic peroxidases. The slides then were washed with phosphate buffer. The slices on the slides were covered with the blocking reagent A included in Histofine immunohistochemical staining reagents (Nichirei) and allowed to stand for 60 minutes at room temperature. After this treatment, the slides were washed with phosphate buffer.

Figure 5:
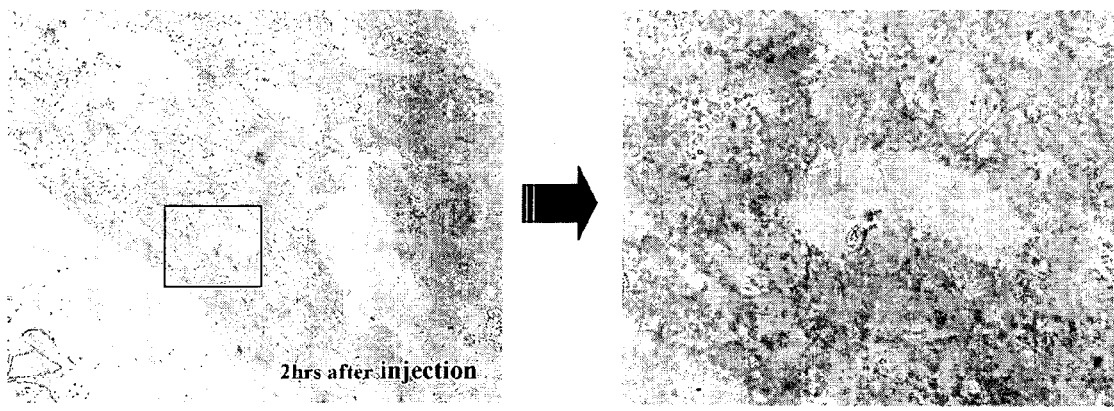
FIG. 5 shows the images of the stained GALNS fusion protein, in comparison with native GALNS, transferred to the myeloid tissue.
Figure 5:
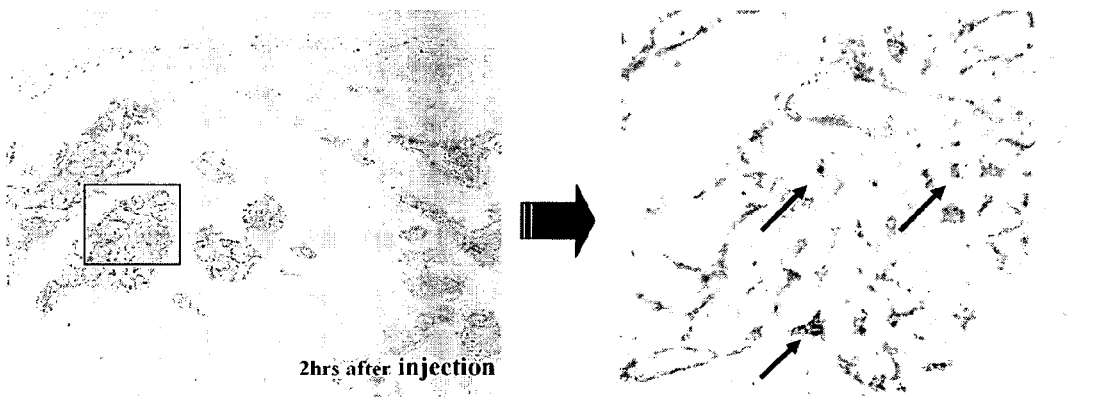

The slices were covered with an anti-GALNS monoclonal antibody solution and allowed to stand for 15 hours at 4° C. After the reaction, the slides were washed with phosphate buffer. The slices on the slides were covered with the blocking reagent B included in Histofine immunohistochemical staining reagents (Nichirei) and allowed to stand for 10 minutes at room temperature. After the treatment, the slides were washed with phosphate buffer. The slices on the slides were covered with SimpleStain Mouse MAX-PO (Mouse) (Nichirei), which was a peroxidase-conjugated secondary antibody against mouse primary antibodies, and allowed to stand for 5 minutes at room temperature. After the reaction, the slides were washed with phosphate buffer. The slices on the slides were covered with SimpleStain DAB solution (Nichirei) and allowed to develop color while monitoring the strength of the color developed under a microscope. The reaction of color-development was stopped by washing with purified water. The result of staining is shown in FIG. 5. While signals of intense stained spots were observed in the myeloid tissue from the mice administered with NBT-GALNS, hardly any signals were observed in the myeloid tissues from the mice administered with native GALNS. The results demonstrate that NBT-GALNS, compared to native GALNS, has remarkable higher transferability to the bone tissue when administered to the circulating blood.

[Method for Measurement of GALNS-Specific Enzyme Activity]

Measurement of GALNS activity in the blood after intravenous administration of native- or NBT-GALNS to mice was performed as follows. Briefly, a 10-μL plasma sample was added to 18 μL of a solution of 10 mM 4-Methylumbelliferyl-beta-D-Galactopyranoside-6-Sulfate (4MUF-Gal-6-S) (Toronto Research Chemicals Inc.) which had been prepared using a determination buffer (100 mM NaCl, 100 mM $CH_3COONa$, pH 4.3), and reaction was allowed for 6 hours at 37° C. Then, 2 μL of 10 mg/mL Beta-Galactosidase solution (SIGMA) which had been prepared using the determination buffer were added, and allowed to react for 1 hour at 37° C. 970 μL of a stop buffer (1 M Glycine-HCl, pH 10.5) then were added and mixed to stop the enzyme reaction. A 200-μL aliquot of the enzyme reaction was transferred to a 96-well plate, and excitation 355 nm/emission 460 nm was measured on a fluorescence plate reader (Molecular Device) fmax.

[Stability in the Blood]

Figure 6:
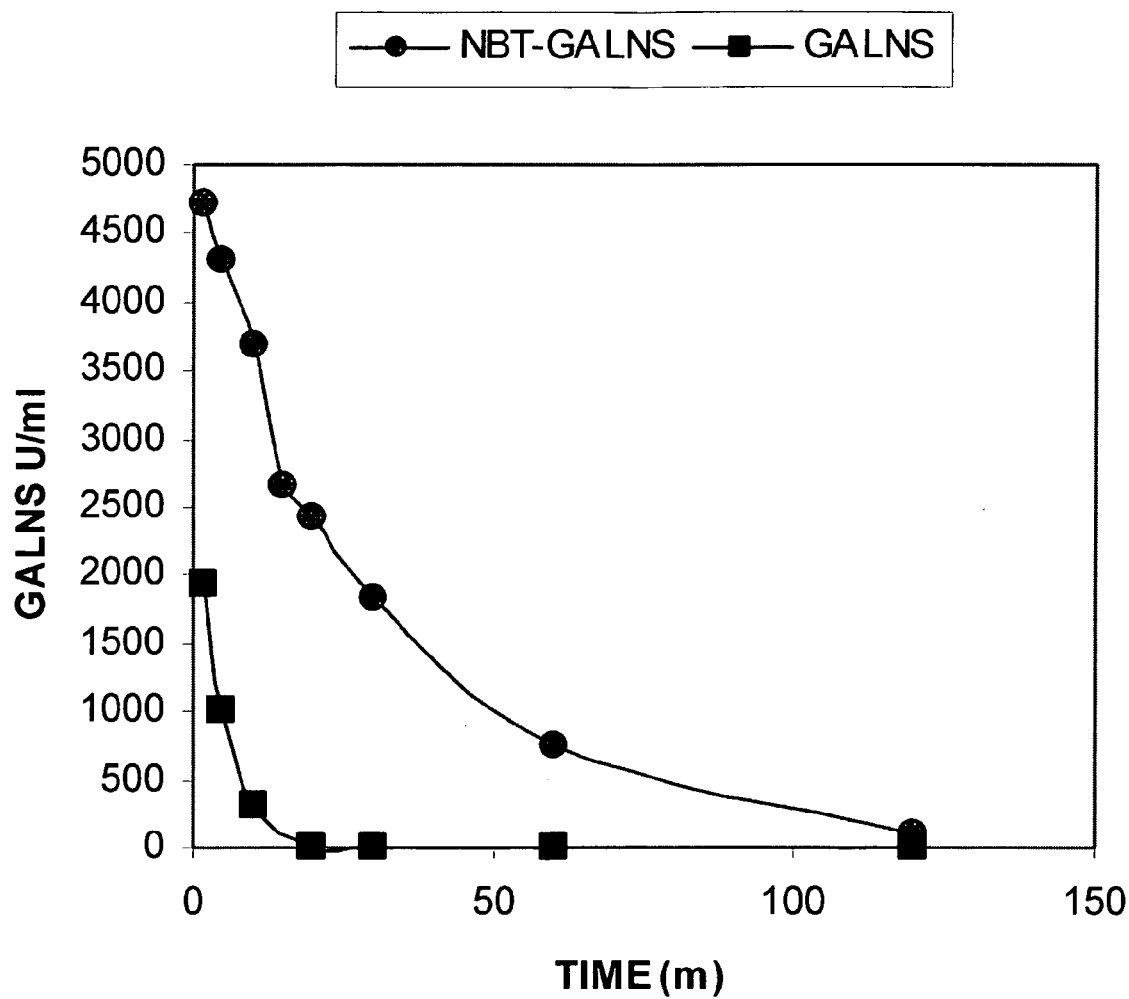
FIG. 6 is a graph showing the time profiles of the blood activity levels of native GALNS and the GALNS fusion protein after they are intravascularly administered in an equivalent amount.

Per 1 g of body weight, 250 U of GALNS or NBT-GALNS, both purified, were administered to 3 male, 4-month old C57BL mice per group in the tail vein. Samples of venous blood were collected at 2, 5, 10, 20, 30, 60 and 120 minutes after the administration, and GALNS activity in the serum was measured. The results are shown in FIG. 6. Comparison between NBT-GLNS-administered group and the native GALNS-administered group revealed that the enzyme activity in the blood at 2 minutes after the administration was 2-fold higher in the NBT-GALNS-administered group than the native GALNS-administered group. And, while the enzyme activity in the blood at 20 minutes after the administration was almost disappeared in the native GALNS-administered group, the NBT-GALNS-administered group retained activity levels, which were even higher than the activity levels found in the native GALNS-administered group at 2 minutes after the administration, and showed much slower reduction of activity afterwards than that found in the native GALNS-administered group. The results demonstrate that the stability of GALNS in the body is remarkably increased by attaching a short peptide of acidic amino acid to native GALNS. To the best of the inventors' knowledge, there was no report indicating that acidic short peptide added to GALNS or other physiologically active proteins improved the stability of such proteins in the body. This finding provides novel means for stabilization of different therapeutically useful enzymes, peptide hormones and other physiologically active proteins in the body after they are administered in the blood.

INDUSTRIAL APPLICABILITY

The present invention enables production of physiologically active proteins which have improved transferability to the bone tissues and increased stability in the body. The present invention also provides method and pharmaceutical composition for treatment of type A Morquio disease.

REFERENCES (1) Bernardi G., Chromatography of proteins on hydroxyapatite, Methods Enzymol. 27:471-9 (1973)

(2) Fujisawa R, Wada Y, Nodasaka Y, Kuboki Y., Acidic amino acid-rich sequences as binding sites of osteonectin to hydroxyapatite crystals, Biochim Biophys Acta 41292:53-60 (1996)

(3) Japanese Patent Application Publication No. 2000-327583

(4) Japanese Patent Application Publication No. 2002-3407

(5) Japanese Patent No. 2852127

(6) Kazuko Yukawa, Shunji Tomatsu, Tadao Orii and Naomi Kondo, Type IV Mucopolysaccharidosis (Morquio Sybdrome), Congenital metabolic disorder syndromes, Japanese Journal of Clinical Medicine, Suppl. No. 2, p. 442-445 (1998)

(7) Niwa H, Yamamura K, Miyazaki J., Efficient selection for high-expression transfectants with a novel eukaryotic vector. Gene 108:193-200 (1991)

(8) Tomatsu S, Fukuda S, Masue M, Sukegawa K, Fukao T, et al., Morquio disease: Isolation, characterization and expression of full-length cDNA for human N-Acetylgalactosamine-6-sulfate sulfatase, Biochem. Biophys. Res. Commun. 181:677-683 (1991)

(9) Rose, T. M, et al., Primary structure of the human melanoma-associated antigen p97 (melanotransferrin) deduced from the mRNA sequence, Proc. Natl. Acad. Sci. USA, 83:1261-1265 (1986)

The invention claimed is:

1. A fusion protein consisting of SEQ ID NO: 7.

2. A pharmaceutical composition comprising a pharmaceutically acceptable carrier and a fusion protein consisting of SEQ ID NO: 7.

3. The fusion protein according to claim 1, which has increased stability in the blood and enhanced transferability from the blood to bone tissues compared with native N-acetylgalactosamine-6-sulfate sulfatase.

4. The pharmaceutical composition according to claim 2, wherein said fusion protein has increased stability in the blood and enhanced transferability from the blood to bone tissues compared with native N-acetylgalactosamine-6-sulfate sulfatase.

5. A fusion protein consisting of amino acids 20-528 of SEQ ID NO: 7.

6. The fusion protein according to claim 1, which has been purified.

7. The fusion protein according to claim 1, which has enhanced in vivo stability compared to native GALNS.

* * * * *

SEQUENCE LISTING

<160> NUMBER OF SEQ ID NOS: 9

<210> SEQ ID NO 1
<211> LENGTH: 1559
<212> TYPE: DNA
<213> ORGANISM: Homo sapiens

<400> SEQUENCE: 1

```
tggcggcggt tgtcgcggcg acgaggtggt ggcagctgtt gctggtgctc agcgccgcgg      60
ggatgggggc ctcgggcgcc ccgcagcccc ccaacatcct gctcctgctc atggacgaca     120
tgggatgggg tgacctcggg gtgtatggag agccctccag agagaccccg aatttggacc     180
ggatggctgc agaagggctg cttttcccaa acttctattc tgccaaccct ctgtgctcgc     240
catcgagggc ggcactgctc acaggacggc tacccatccg caatggcttc tacaccacca     300
acgcccatgc cagaaacgcc tacacaccgc aggagattgt gggcggcatc ccagactcgg     360
agcagctcct gccggagctt ctgaagaagg ccggctacgt cagcaagatt gtcggcaagt     420
ggcatctggg tcacaggccc cagttccacc ccctgaagca cggatttgat gagtggtttg     480
gatcccccaa ctgccacttt ggaccttatg acaacaaggc caggcccaac atccctgtgt     540
acagggactg ggagatggtt ggcagatatt atgaagaatt cctattaat ctgaagacgg     600
gggaagccaa cctcacccag atctacctgc aggaagccct ggacttcatt aagagacagg     660
cacggcacca ccccttttc ctctactggg ctgtcgacgc cacgcatgca cccgtctatg     720
cctccaaacc cttcttgggc accagtcagc gagggcggta tggagacgcc gtccgggaga     780
ttgatgacag cattgggaag atactggagc tcctccaaga cctgcacgtc gcggacaaca     840
ccttcgtctt cttcacgtcg gacaacggcg ctgccctcat ttccgccccc gaacaaggtg     900
gcagcaacgg cccctttctg tgtgggaagc agaccacgtt tgaaggaggg atgagggagc     960
ctgccctcgc atggtggcca gggcacgtca ctgcaggcca ggtgagccac cagctgggca    1020
gcatcatgga cctcttcacc accagcctgg cccttgcggg cctgacgccg cccagcgaca    1080
gggccattga tggcctcaac ctcctcccca ccctcctgca gggccggctg atggacaggc    1140
ctatcttcta ttaccgtggc gacacgctga tggcggccac cctcgggcag cacaaggctc    1200
acttctggac ctgaccaac tcctgggaga acttcagaca gggcattgat ttctgccctg    1260
ggcagaacgt ttcaggggtc acaactcaca atctggaaga ccacgaag ctgcccctga    1320
tcttccacct gggacgggac ccaggggaga ggttcccct cagctttgcc agcgccgagt    1380
accaggaggc cctcagcagg atcacctcgg tcgtccagca gcaccaggaa gccttggtcc    1440
ccgcgcagcc ccagctcaac gtgtgcaact gggcggtcat gaactgggca cctccgggct    1500
gtgaaaagtt agggaagtgt ctgacacctc cagaatccat tcccaagaag tgcctctgg     1559
```

<210> SEQ ID NO 2
<211> LENGTH: 66
<212> TYPE: DNA
<213> ORGANISM: Homo sapiens

<400> SEQUENCE: 2

```
tgatcagaag aggaagagga agaggccgag gcagaaaccg gtgccccgca gccccccaac      60
atcctg                                                                66
```

<210> SEQ ID NO 3
<211> LENGTH: 45

```
<212> TYPE: DNA
<213> ORGANISM: Homo sapiens

<400> SEQUENCE: 3
tctagagaat tcctcgagct agtgggacca gaggcacttc ttggg              45

<210> SEQ ID NO 4
<211> LENGTH: 50
<212> TYPE: DNA
<213> ORGANISM: Homo sapiens

<400> SEQUENCE: 4
attaggtacc tgatcagaag aggaggaaga agaggccgag gcagaaaccg         50

<210> SEQ ID NO 5
<211> LENGTH: 25
<212> TYPE: DNA
<213> ORGANISM: Homo sapiens

<400> SEQUENCE: 5
tgcggggcac cggtttctgc ctcgg                                    25

<210> SEQ ID NO 6
<211> LENGTH: 1611
<212> TYPE: DNA
<213> ORGANISM: Artificial
<220> FEATURE:
<223> OTHER INFORMATION: Part of sequence of pCXN-p97-NBT-GALNS
      containing NBT-GALNS cDNA. Nt13-69 encode p97 signal sequence,
      nt73-90 poly Glu, nt91-108 linker sequence, and nt109-1596 GALNS
      without signal sequence.

<400> SEQUENCE: 6
gaattcaccg ccatgcgggg tccgagcggg gctctgtggc tgctcctggc tctgcgcacc    60
gtgctcggat cagaagagga ggaagaagag gccgaggcag aaaccggtgc cccgcagccc   120
cccaacatcc tgctcctgct catggacgac atgggatggg gtgacctcgg ggtgtatgga   180
gagccctcca gagaccccc gaatttggac cggatggctg cagaagggct gcttttccca   240
aacttctatt ctgccaaccc tctgtgctcg ccatcgaggg cggcactgct cacaggacgg   300
ctacccatcc gcaatggctt ctacaccacc aacgcccatg ccagaaacgc ctacacaccg   360
caggagattg tgggcggcat cccagactcg gagcagctcc tgccggagct tctgaagaag   420
gccggctacg tcagcaagat tgtcggcaag tggcatctgg gtcacaggcc ccagttccac   480
cccctgaagc acggatttga tgagtggttt ggatccccca ctgccacttt ggaccttat   540 gacaacaagg ccaggcccaa catccctgtg tacagggact gggagatggt tggcagatat   600
tatgaagaat tcctattaa ctgaagacg ggggaagcca acctcaccca gatctacctg   660
caggaagccc tggacttcat taagagacag gcacggcacc cccctttt cctctactgg   720 gctgtcgacg ccacgcatgc acccgtctat gcctccaaac ccttcttggg caccagtcag   780
cgagggcggt atggagacgc cgtccgggag attgatgaca gcattgggaa gatactggag   840
ctcctccaag acctgcacgt cgcggacaac accttcgtct tcttcacgtc ggacaacggc   900
gctgccctca tttccgcccc cgaacaaggt ggcagcaacg gccccttct gtgtgggaag   960 cagaccacgt tgaaggagg gatgagggag cctgccctcg catggtggcc agggcacgtc   1020
actgcaggcc aggtgagcca ccagctgggc agcatcatgg acctcttcac caccagcctg   1080
gcccttgcgg gcctgacgcc gcccagcgac agggccattg atggcctcaa cctcctcccc   1140
accctcctgc agggccggct gatggacagg cctatcttct attaccgtgg cgacacgctg   1200
```

```
atggcggcca ccctcgggca gcacaaggct cacttctgga cctggaccaa ctcctgggag    1260
aacttcagac agggcattga tttctgccct gggcagaacg tttcaggggt cacaactcac    1320
aatctggaag accacacgaa gctgccctg atcttccacc tgggacggga cccaggggag     1380
aggttccccc tcagctttgc cagcgccgag taccaggagg ccctcagcag gatcacctcg    1440
gtcgtccagc agcaccagga agccttggtc cccgcgcagc cccagctcaa cgtgtgcaac    1500
tgggcggtca tgaactgggc acctccgggc tgtgaaaagt tagggaagtg tctgacacct    1560
ccagaatcca ttcccaagaa gtgcctctgg tcccactagc tcgaggaatt c             1611
```

<210> SEQ ID NO 7
<211> LENGTH: 528
<212> TYPE: PRT
<213> ORGANISM: Artificial
<220> FEATURE:
<223> OTHER INFORMATION: NBT-GALNS with p97 signal sequence. Aa1-19: p97 signal sequence, aa21-26: poly Glu, aa 27-32: linker sequence, aa33-528: GALNS without signal sequence.

<400> SEQUENCE: 7

```
Met Arg Gly Pro Ser Gly Ala Leu Trp Leu Leu Leu Ala Leu Arg Thr
1               5                   10                  15

Val Leu Gly Ser Glu Glu Glu Glu Glu Ala Glu Ala Glu Thr Gly
            20                  25                  30

Ala Pro Gln Pro Pro Asn Ile Leu Leu Leu Met Asp Asp Met Gly
            35                  40                  45

Trp Gly Asp Leu Gly Val Tyr Gly Glu Pro Ser Arg Glu Thr Pro Asn
    50                  55                  60

Leu Asp Arg Met Ala Ala Glu Gly Leu Leu Phe Pro Asn Phe Tyr Ser
65                  70                  75                  80

Ala Asn Pro Leu Cys Ser Pro Ser Arg Ala Ala Leu Leu Thr Gly Arg
                85                  90                  95

Leu Pro Ile Arg Asn Gly Phe Tyr Thr Thr Asn Ala His Ala Arg Asn
            100                 105                 110

Ala Tyr Thr Pro Gln Glu Ile Val Gly Gly Ile Pro Asp Ser Glu Gln
            115                 120                 125

Leu Leu Pro Glu Leu Leu Lys Lys Ala Gly Tyr Val Ser Lys Ile Val
130                 135                 140

Gly Lys Trp His Leu Gly His Arg Pro Gln Phe His Pro Leu Lys His
145                 150                 155                 160

Gly Phe Asp Glu Trp Phe Gly Ser Pro Asn Cys His Phe Gly Pro Tyr
                165                 170                 175

Asp Asn Lys Ala Arg Pro Asn Ile Pro Val Tyr Arg Asp Trp Glu Met
            180                 185                 190

Val Gly Arg Tyr Tyr Glu Glu Phe Pro Ile Asn Leu Lys Thr Gly Glu
            195                 200                 205

Ala Asn Leu Thr Gln Ile Tyr Leu Gln Glu Ala Leu Asp Phe Ile Lys
        210                 215                 220

Arg Gln Ala Arg His His Pro Phe Phe Leu Tyr Trp Ala Val Asp Ala
225                 230                 235                 240

Thr His Ala Pro Val Tyr Ala Ser Lys Pro Phe Leu Gly Thr Ser Gln
                245                 250                 255

Arg Gly Arg Tyr Gly Asp Ala Val Arg Glu Ile Asp Asp Ser Ile Gly
            260                 265                 270

Lys Ile Leu Glu Leu Leu Gln Asp Leu His Val Ala Asp Asn Thr Phe
```

-continued

```
                275                 280                 285
Val Phe Phe Thr Ser Asp Asn Gly Ala Ala Leu Ile Ser Ala Pro Glu
            290                 295                 300

Gln Gly Gly Ser Asn Gly Pro Phe Leu Cys Gly Lys Gln Thr Thr Phe
305                 310                 315                 320

Glu Gly Gly Met Arg Glu Pro Ala Leu Ala Trp Trp Pro Gly His Val
                325                 330                 335

Thr Ala Gly Gln Val Ser His Gln Leu Gly Ser Ile Met Asp Leu Phe
            340                 345                 350

Thr Thr Ser Leu Ala Leu Ala Gly Leu Thr Pro Pro Ser Asp Arg Ala
355                 360                 365

Ile Asp Gly Leu Asn Leu Leu Pro Thr Leu Leu Gln Gly Arg Leu Met
            370                 375                 380

Asp Arg Pro Ile Phe Tyr Tyr Arg Gly Asp Thr Leu Met Ala Ala Thr
385                 390                 395                 400

Leu Gly Gln His Lys Ala His Phe Trp Thr Trp Thr Asn Ser Trp Glu
                405                 410                 415

Asn Phe Arg Gln Gly Ile Asp Phe Cys Pro Gly Gln Asn Val Ser Gly
            420                 425                 430

Val Thr Thr His Asn Leu Glu Asp His Thr Lys Leu Pro Leu Ile Phe
                435                 440                 445

His Leu Gly Arg Asp Pro Gly Glu Arg Phe Pro Leu Ser Phe Ala Ser
450                 455                 460

Ala Glu Tyr Gln Glu Ala Leu Ser Arg Ile Thr Ser Val Val Gln Gln
465                 470                 475                 480

His Gln Glu Ala Leu Val Pro Ala Gln Pro Gln Leu Asn Val Cys Asn
                485                 490                 495

Trp Ala Val Met Asn Trp Ala Pro Pro Gly Cys Glu Lys Leu Gly Lys
            500                 505                 510

Cys Leu Thr Pro Pro Glu Ser Ile Pro Lys Lys Cys Leu Trp Ser His
            515                 520                 525
```

<210> SEQ ID NO 8
<211> LENGTH: 52
<212> TYPE: DNA
<213> ORGANISM: Artificial
<220> FEATURE:
<223> OTHER INFORMATION: Forward primer 5. Nt1-5: random synthetic
      sequence, nt6-52: part of sequence encoding p97 signal

<400> SEQUENCE: 8
gtaccgaatt caccgccatg cggggtccga gcggggctct gtggctgctc ct          52

<210> SEQ ID NO 9
<211> LENGTH: 51
<212> TYPE: DNA
<213> ORGANISM: Artificial
<220> FEATURE:
<223> OTHER INFORMATION: Reverse primer 6. Nt1-6: random synthetic
      sequence, nt7-51: part of sequence encoding p97 signal

<400> SEQUENCE: 9
gtaccgggat ccgagcacgg tgcgcagagc caggagcagc cacagagccc c           51